(12) United States Patent
Lau et al.

(10) Patent No.: US 6,864,061 B2
(45) Date of Patent: Mar. 8, 2005

(54) METHOD FOR SCREENING COMPOUNDS FOR ANTI-INFLAMMATORY ACTIVITY

(75) Inventors: Allan S. Lau, Pok Fu Lan (HK); Michael C. Kiefer, Clayton, CA (US)

(73) Assignee: GeneTrol Biotherapeutics, Inc., Oakland, CA (US)

(*) Notice: Subject to any disclaimer, the term of this patent is extended or adjusted under 35 U.S.C. 154(b) by 0 days.

(21) Appl. No.: 09/952,571

(22) Filed: Sep. 13, 2001

(65) Prior Publication Data

US 2002/0123075 A1 Sep. 5, 2002

Related U.S. Application Data

(60) Provisional application No. 60/232,385, filed on Sep. 14, 2000.

(51) Int. Cl.$^7$ ............... G01N 33/53; G01N 33/567; C12N 5/10; C12N 15/12; C12N 15/63
(52) U.S. Cl. ............... 435/7.1; 435/7.2; 435/7.21; 435/325; 435/69.1; 435/471; 435/252.3; 435/320.1
(58) Field of Search ............... 435/6, 7.1, 7.2, 435/7.21, 325, 69.1, 471, 252.3, 320.1

(56) References Cited

U.S. PATENT DOCUMENTS

| | | | |
|---|---|---|---|
| 5,474,897 A | * | 12/1995 | Weiss et al. ............... 435/6 |
| 5,976,800 A | | 11/1999 | Lau et al. |
| 6,030,834 A | * | 2/2000 | Chu et al. ............... 435/325 |
| 6,033,674 A | | 3/2000 | Jaffee et al. |
| 6,159,712 A | | 12/2000 | Lau et al. |
| 2001/0031859 A1 | | 10/2001 | Lau et al. |

FOREIGN PATENT DOCUMENTS

| | | |
|---|---|---|
| WO | WO 97/08292 | 3/1997 |
| WO | WO 97/08324 | 3/1997 |
| WO | WO 98/00013 | 1/1998 |
| WO | WO 00/77236 A2 | 12/2000 |
| WO | WO 01/18185 A1 | 3/2001 |
| WO | WO 02/22848 A2 | 3/2002 |
| WO | WO 02/059281 A2 | 8/2002 |

OTHER PUBLICATIONS

Balachandran et al., *EMBO J.*, 17(23):6888–6902 (19898).
Der, et al., *Proc. Natl. Acad. Sci. USA*, 92:8841–8845 (1995).
Jagus, R., et al., *Int'l. Jour. Biochem. and Cell Biol.*, 31:123–138, (1999).

* cited by examiner

*Primary Examiner*—Prema Mertz
(74) *Attorney, Agent, or Firm*—Peter J. Dehlinger; Perkins Coie LLP

(57) ABSTRACT

A method and cell line for screening test compounds for anti-inflammatory activity are disclosed. The cell line is a human cell line capable of producing a selected cytokine associated with an inflammatory response in humans, and transfected with (i) a vector containing DNA encoding a cytokine regulatory factor under the control of a first promoter, and (ii) a vector containing DNA encoding a detectable-marker protein, under the control of a second promoter which is responsive to cytokine induction. In the screening method, the cells are cultured under conditions of cytokine regulatory factor overexpression and cytokine induction. Addition of test compound that results in a diminution of the detectable-marker protein is evidence of anti-inflammatory activity.

8 Claims, 6 Drawing Sheets

| Cytokine | Promoter | Genbank |
|---|---|---|
| TNF-beta | gccctggggg cttccccggg c | |
| IL-1(RI) | 1 ctcattggca aagtgagctg gtgggcataa gtgggtttta agtttaaaaa tttaaaaacc<br>61 ctgtctgccc ccaagtgtgg tatcaagatt ttataglatg acacttaaat tgctttttc<br>121 atccgggcgc gtaacagcaa caatgaaacc agcagataac gcgtgagtag tatcagctct<br>181 gggcctggca ctattttata tgtattagct catttttttt aaaaaactgt tttcaaccac<br>241 tccatgagat gagtgctctt atgatcccft tttcacagaa gcggaaacgg aggtacaaag<br>301 aaattagtgc acaaagccag tcggagagag ccccctggcca ggcaccaagc tccagaggtc<br>361 gctctggcga gcgtttgctt cgggatctga tgccctggag tgccaaactc aattcgcggt<br>421 cgcagccagg ctccatgggg gtagtagagc caggtcgtag tggctaggtg agttgtctca<br>481 actaactcta gtggagccgc cgcagcccctg gaggagccgg gccagccgac tcgagagcgc<br>541 ccggcagctc tccaatgctt tggaaccggc gggacccctg cggctacccg gggcagggcg<br>601 gtgtccgagg ggtctgtcca gccgcgcctg ctcctcggtg gagagtggaa cccggccagc<br>661 tcgctcgcag cccgcgactg cccagcgagc gtctcgccgt tccccgcccc cgcagcggcg<br>721 gctagagcga gaccgcgaaa ggcagttccc ggccggaggg ccgcagcttg tggccggcgc<br>781 cggagccgac tcggagcgcg cggcgcggcc gggaggagcc gagcgcgccg ggcgcggcgt | L09701 |
| IL-6 | 1 ttgtcaagac atgccaaagt gctgagtcac taataaaaga aaaaagaaa gtaaaggaag<br>61 agtggttctg cttcttagcg ctagcctcaa tgacgaccta agctgcactt ttcccctag<br>121 ttgtgtcttg ccatgctaaa ggacgtcaca ttgcacaatc ttaataaggt ttccaatcag<br>181 ccccaccccgc tctggcccca ccctcaccct ccaacaaaga tttatcaaat gtgggatttt<br>241 cccatgagtc tcaatattag agtctcaacc cccaataaat ataggactgg agatgtctga<br>301 ggc | AF005485 |
| IL-8(RB) promoter 1 | 1 aagcttacct cattctctcg tggggtactc tttatttatt tatttaattt ttccccagta<br>61 ttttacttac tgagttgatg attcaggctt tggaccagta ggggaagtat ccctgggtag<br>121 gcaccagatg tagctaaagt aggtgggtag gcaccggttg tagctaaagc aggtgggcag<br>181 agatcccagc cttgatgaga gtgcctggga gagctctcaa ttagatgtgc tgaggtttg<br>241 tcagggtgaa gggtaggagc taccctcaggt cccccactag gccagctgga aagctatcca<br>301 cctcccagct tcactccttt cccagtgttc cagctattca gatcagacag gcagttattt<br>361 tcatctgtag aaatgttgat gttccaagta gagaggaatt gtgactgcct gtcatgcaaa<br>421 cctgaatctg gggagtgctc ctcccgtggg gatgcaatca ccctgatttg ttccaggaag<br>481 gctgtctata ggtgcatcaa tgctgcgttc ctttgggaga ccccagct ctgtctgcag<br>541 tggcgtacca gggggaacaa ggatccctc tctaagaccc ttcacaatac cagaggctgc<br>601 ctgcctattg ggtagaggtg caaactttcc cccactctgc ccagcacagc aattgtctct<br>661 gcaataggaa acttcccacc agtgaaaaga tctgggactc aagccctgcc attcagattc<br>721 ttttgttcca cagggtattc ccttgatgtg atgttcttcc ccttcctcta ggaatgggac<br>781 ttcctggaag ccagactaca gtgctcttct gggctctcc acccagtggg cctaccagac | U11866 |
| IL-8(RB) promoter 2 | 1114 tctcctt cctgggtaca gtgctattct<br>1141 gcctagaggt gagttttgc ctgtctcaca gagtaggctg cagcctgcca cttctttcaa<br>1201 aagttctgtg gattcttca gctttcctgt tcagttcctg cattcgttcc tggagaaaaa<br>1261 aaaattatag tgtgaatctc tacacgctat tctgtccttc cagatgggag aggcatgcta<br>1321 atgctgcctc caatctgttg tcttggggggg aaagaaaaca atttgttttg ttttttttt<br>1381 aatggatttg ctgggtttag taacccagag gtcattggga accttggcga aagttatttc<br>1441 agtggagcag taggaaggaa gccagttgca gtgtcttttgt tgagcagcag aggggaggtg<br>1501 aggaagtgga gagagcagct gtggtggctg aagggtgcta ggacagaggg agcatgataa<br>1561 agccataagt aagatgtggt agaagggaaa gagccaggac agaggggaga gaaagcagga<br>1621 tcctcaagga ccagagaggc agtgggtcct acagtcaggt gcggggattc aacagaaaca<br>1681 gaaggaggga cgcttctcac tctgaccccg gaaagaagga agaaactgcg tgcgagttca<br>1741 gacaagtccg ttggcggggg ctgggatgcc tgcatcttcc ttgttaaaaa aggaagtgca<br>1801 ggttcaaaac attcagagac agaaggtgga tagacaaatc tccaccttca gactggtagg<br>1861 ctcctccaga agccatcaga ca | U11866 |

Figure 5A

| | | |
|---|---|---|
| IL-8(RA) | 1 aagcttccac aggtgatata ctaggaatt taggaataaa caaatgaaa taaattcaag<br>61 aaaaggaaaa taataaaaat gatcatccat agagtggaga attcagataa tggaccctca<br>121 accccagctt cacacctggg acccccactt ggtcatatgg acctggcag tctctaatca<br>181 caagtctgtg atcccttgac ttaaactgtt cttcccaaa tgtagacatg ggtggggctc<br>241 agaaggagg tgtcatctga tgtgttcc ttattcatca agtgccctct | U11870 |
| IFN-beta | agggtatcta catgagctac | E00218 |
| IFN-gamma (ovine) | 1 ggatcccaca agaatggcat gggtgggcat aatgggtctg tctcctcgtc aaaagaccca<br>61 aggagttgaa aggaaactct aactacaaga ccaaaatgcc acaaaaccat agttattaat<br>121 accaactaac tagcatctct gtctatctgt caccactca tcttaaaaaaa cttgtgaaaa<br>181 tacgtaatct tgatgagact tcaattaggt ataaatacc | Z92887 |
| TNF-alpha | 1 ggggaagcaa agagaagct gagagagtga agaaaagtc agggtctgga gggggcgggg<br>61 tcagggagct cctgggagat atgccacat gtagcggctc tgaggaatgg gttacaggag<br>121 acctctgggg agatgtgacc acagcaatgg gtaggagaat gtccagggct atggaagtcg<br>181 agtatcgggg acccccctt aacgaagaca gggccatgta gaggccccca gggagtgaaa<br>241 gagcctccag gacctccagg tatgaatac agggacgtt taagaagata tggccacaca<br>301 ctggggccct gagaagtgag agcttcatga aaaaatcag ggaccccaga gttccttgga<br>361 agccaagact gaaaccagca ttatgagtct ccgggtcaga atgaaagaag aaggcctgcc<br>421 ccagtggtct gtgaattccc gggggtgatt tcactcccg ggctgtccca ggcttgtccc<br>481 tgctacccc accagcctt tcctgaggcc tcaagctgcc accaagcccc cagtcctc<br>541 tccccgcaga cccaaacaca ggcctcagga ctcaacacag ctttcctc caacccgtt<br>601 ttctctccct caaggactca gctttctgaa gcccctccca gttctagttc tatctttc<br>661 ctgcatcctg tctggaagtt agaaggaaac agaccacaga cctggtcccc aaaagaaatg<br>721 gaggcaatag gttttgaggg gcatgggac gggttcagc ctcagggtc ctacacaca<br>781 atcagtcagt ggccccagaag accccctcg gaatcggaag aggaggatg gggagtgtga | L11698 |

Figure 5B

SEQUENCE LISTING

<160> NUMBER OF SEQ ID NOS: 9

<210> SEQ ID NO 1
<211> LENGTH: 21
<212> TYPE: DNA
<213> ORGANISM: Homo sapiens

<400> SEQUENCE: 1
gccctggggg cttccccggg c                                        21

<210> SEQ ID NO 2
<211> LENGTH: 840
<212> TYPE: DNA
<213> ORGANISM: Homo sapiens

<400> SEQUENCE: 2
ctcattggca aagtgagctg gtgggcataa gtgggtttta agtttaaaaa tttaaaaacc    60

| | |
|---|---|
| ctgtctgccc ccaagtgtgg tatcaagatt ttatagtatg acacttaaat tgctttttc | 120 |
| atccgggcgc gtaacagcaa caatgaaacc agcagataac gcgtgagtag tatcagctct | 180 |
| gggcctggca ctattttata tgtattagct cattttttt aaaaaactgt tttcaaccac | 240 |
| tccatgagat gagtgctctt atgatccctt tttcacagaa gcggaacgg aggtacaaag | 300 |
| aaattagtgc acaaagccag tcggagagag cccctggcca ggcaccaagc tccagaggtc | 360 |
| gctctggcga gcgtttgctt cgggatctga tgccctggga tgccaaactc aattcgcggt | 420 |
| cgcagccagg ctccatgggg gtagtagagc caggtcgtag tggctaggtg agttgtctca | 480 |
| actaactcta gtggagccgc cgcagccctg gaggagccgg ccagccgac tcgagagcgc | 540 |
| ccggcagctc tccaatgctt tggaaccggc gggacccctg cggctacccg ggcagggcg | 600 |
| gtgtccgagg ggtctgtcca gccgcgcctg ctcctcggtg gagagtggaa cccggccagc | 660 |
| tcgctcgcag cccgcgactg cccagcgagc gtctcgccgt tccccgcccc cgcagcggcg | 720 |
| gctagagcga gaccgcgaaa ggcagttccc ggccggaggg ccgcagcttg tggccggcgc | 780 |
| cggagccgac tcggagcgcg cggcgcggcc gggaggagcc gagcgcgccg ggcgcggcgt | 840 |

<210> SEQ ID NO 3
<211> LENGTH: 303
<212> TYPE: DNA
<213> ORGANISM: Homo sapiens

<400> SEQUENCE: 3

| | |
|---|---|
| ttgtcaagac atgccaaagt gctgagtcac taataaaaga aaaaagaaa gtaaaggaag | 60 |
| agtggttctg cttcttagcg ctagcctcaa tgacgaccta agctgcactt ttcccctag | 120 |
| ttgtgtcttg ccatgctaaa ggacgtcaca ttgcacaatc ttaataaggt ttccaatcag | 180 |
| ccccacccgc tctgccccca ccctcaccct ccaacaaaga tttatcaaat gtgggatttt | 240 |
| cccatgagtc tcaatattag agtctcaacc cccaataaat ataggactgg agatgtctga | 300 |
| ggc | 303 |

<210> SEQ ID NO 4
<211> LENGTH: 840
<212> TYPE: DNA
<213> ORGANISM: Homo sapiens

<400> SEQUENCE: 4

| | |
|---|---|
| aagcttacct cattctctcg tgggtactc tttatttatt tatttaattt ttccccagta | 60 |
| ttttacttac tgagttgatg attcaggctt tggaccagta ggggaagtat ccctgggtag | 120 |
| gcaccagatg tagctaaagt aggtgggtag gcaccggttg tagctaaagc aggtgggcag | 180 |
| agatcccagc cttgatgaga gtgcctggga gagctctcaa ttagatgtgc tgaggttttg | 240 |
| tcagggtgaa gggtaggagc tacctcaggt cccccactag gccagctgga aagctatcca | 300 |
| cctcccagct tcactccttt cccagtgttc agctattca gatcagacag gcagttattt | 360 |
| tcatctgtag aaatgttgat gttccaagta gagaggaatt gtgactgcct gtcatgcaaa | 420 |
| cctgaatctg gggagtgctc ctcccgtggg gatgcaatca ccctgatttg ttccaggaag | 480 |
| gctgtctata ggtgcatcaa tgctgcgttc ctttgggaga agcccagct ctgtctgcag | 540 |
| tggcgtacca gggggaacaa ggatcccttc tctaagaccc ttcacaatac cagaggctgc | 600 |
| ctgcctattg ggtagaggtg caaactttcc cccactctgc ccagcacagc aattgtctct | 660 |
| gcaataggaa acttcccacc agtgaaaaga tctgggactc aagccctgcc attcagattc | 720 |
| ttttgttcca cagggtattc ccttgatgtg atgttcttcc ccttcctcta ggaatgggac | 780 |

```
ttcctggaag ccagactaca gtgctcttct gggtctagcc acccagtggg cctaccagac    840

<210> SEQ ID NO 5
<211> LENGTH: 769
<212> TYPE: DNA
<213> ORGANISM: Homo sapiens

<400> SEQUENCE: 5
tctccttcct gggtacagtg ctattctgcc tagaggtgag ttttgcctg tctcacagag     60 taggctgcag cctgccactt ctttcaaaag ttctgtggat tctttcagct ttcctgttca   120
gttcctgcat tcgttcctgg agaaaaaaaa attatagtgt gaatctctac acgctattct   180
gtccttccag atgggagagg catgctaatg ctgcctccaa tctgttgtct tgggggaaa    240 gaaaacaatt tgttttgttt ttttttaat ggatttgctg ggtttagtaa cccagaggtc    300
attgggaacc ttggcgaaag ttatttcagt ggagcagtag gaaggaagcc agttgcagtg   360
tctttgttga gcagcagagg ggaggtgagg aagtggagag agcagctgtg gtggctgaag   420
ggtgctagga cagagggagc atgataaagc cataagtaag atgtggtaga agggaaagag   480
ccaggacaga ggggagagaa agcaggatcc tcaaggacca gagaggcagt gggtcctaca   540
gtcaggtgcg gggattcaac agaaacagaa ggagggacgc ttctcactct gaccccggaa   600
agaaggaaga aactgcgtgc gagttcagac aagtccgttg gcgggggctg ggatgcctgc   660
atcttccttg ttaaaaaagg aagtgcaggt tcaaaacatt cagagacaga aggtggatag   720
acaaatctcc accttcagac tggtaggctc ctccagaagc catcagaca               769

<210> SEQ ID NO 6
<211> LENGTH: 300
<212> TYPE: DNA
<213> ORGANISM: Homo sapiens

<400> SEQUENCE: 6
aagcttccac aggtgatata ctagggaatt taggaataaa caaatggaaa taaattcaag    60
aaaaggaaaa taataaaaat gatcatccat agagtggaga attcagataa tggaccctca   120
accccagctt cacacctggg acccccactt ggtcatatgg accctggcag tctctaatca   180
caagtctgtg atcccttgac ttaaactgtt cttccccaaa tgtagacatg ggtgggctc    240 agaagggagg tgtcatctga tgtggtttcc ttatttccgt ttattcatca agtgccctct   300

<210> SEQ ID NO 7
<211> LENGTH: 20
<212> TYPE: DNA
<213> ORGANISM: Homo sapiens

<400> SEQUENCE: 7
agggtatcta catgagctac                                                20

<210> SEQ ID NO 8
<211> LENGTH: 219
<212> TYPE: DNA
<213> ORGANISM: Ovis aries

<400> SEQUENCE: 8
ggatcccaca agaatggcat gggtgggcat aatgggtctg tctcctcgtc aaaagaccca    60
aggagttgaa aggaaactct aactacaaga ccaaaatgcc acaaaccat agttattaat    120 accaactaac tagcatctct gtctatctgt caccatctca tcttaaaaaa cttgtgaaaa   180
```

-continued

```
tacgtaatct tgatgagact tcaattaggt ataaatacc                              219

<210> SEQ ID NO 9
<211> LENGTH: 840
<212> TYPE: DNA
<213> ORGANISM: Homo sapiens

<400> SEQUENCE: 9
ggggaagcaa aggagaagct gagaagatga aggaaaagtc agggtctgga ggggcggggg        60
tcagggagct cctgggagat atggccacat gtagcggctc tgaggaatgg gttacaggag      120
acctctgggg agatgtgacc acagcaatgg gtaggagaat gtccagggct atggaagtcg      180
agtatcgggg acccccctt aacgaagaca gggccatgta gagggcccca gggagtgaaa      240
gagcctccag gacctccagg tatggaatac aggggacgtt taagaagata tggccacaca      300
ctggggccct gagaagtgag agcttcatga aaaaaatcag ggaccccaga gttccttgga      360
agccaagact gaaaccagca ttatgagtct ccgggtcaga atgaaagaag aaggcctgcc      420
ccagtggtct gtgaattccc gggggtgatt tcactcccg ggctgtccca ggcttgtccc      480 tgctacccc acccagcctt tcctgaggcc tcaagctgcc accaagcccc cagctccttc      540
tccccgcaga cccaaacaca ggcctcagga ctcaacacag cttttccctc caacccgtt      600 ttctctccct caaggactca gctttctgaa gcccctccca gttctagttc tatcttttc      660 ctgcatcctg tctggaagtt agaaggaaac agaccacaga cctggtcccc aaaagaaatg      720
gaggcaatag gttttgaggg gcatgggac ggggttcagc ctccagggtc ctacacacaa      780
atcagtcagt ggcccagaag accccctcg gaatcggagc agggaggatg gggagtgtga      840
```

METHOD FOR SCREENING COMPOUNDS FOR ANTI-INFLAMMATORY ACTIVITY

This application claims priority to U.S. Provisional Patent Application Ser. No. 60/232,385 filed on Sep. 14, 2000, which is incorporated herein in its entirety by reference.

FIELD OF THE INVENTION

The present invention relates to a method, cell composition and assay for screening compounds for anti-inflammatory activity in vitro by suppressing cytokine regulatory factor-mediated induction of proinflammatory cytokines.

BACKGROUND OF THE INVENTION

The double stranded RNA (dsRNA)-activated protein kinase PKR, also referred to as P1/elF2 kinase, dsRNA-activated inhibitor (DAI or dsI), and p68 (human) or p65 (murine) kinase, is a ubiquitously expressed serine/threonine protein kinase that was initially identified as an interferon (IFN)-induced protein and characterized as a translational inhibitor in an antiviral pathway regulated by IFNs (reviewed in Stark, G. R., et al., *Ann. Rev. Biochem.* 67:227–264, (1998)).

PKR has been shown to play a variety of important roles by regulating translation, transcription and signal transduction pathways through its ability to phosphorylate various intracellular proteins. One well characterized role of PKR is the phosphorylation of eukaryotic initiation factor 2 alpha-subunit (elF-2alpha), which once phosphorylated, ultimately leads to inhibition of cellular and viral protein synthesis Hershey, J. W. B., *Ann. Rev. Biochem.* 60:717–755, (1991)).

In addition to mediating the antiviral activities of IFN-alphas, PKR has more recently been implicated in other aspects of cellular function including normal growth control, induction of apoptosis and signal transduction (Williams, B. R. G., *Biochem. Soc, Trans.* 25:509–513, (1997); Yeug, M. C., et al., *Proc. Natl. Acad. Sci., USA* 93:12451–12455, (1996)). Its role as a signal transducer has been established for dsRNA, lipopolysaccharide (LPS) and the proinflammatory cytokines, tumor necrosis factor (TNF), interleukin-1beta and IFN-gamma. PKR has been shown to mediate signal transduction through activation of important transcription factors such as nuclear factor kappa B (NF-κB), activating transcription factor-2 (ATF-2), signal transducer and activator of transcription-1 (STAT-1) and interferon regulatory factor-1 (IRF-1) Williams B. R. G., *Oncopene* 18:6112–6120, (1999)).

When PKR is overexpressed in cells and subsequently activated by dsRNA, it results in increased production of the antiviral cytokines IFN-alpha and IFN-beta, the proinflammatory cytokines TNF-beta and IL-6 and the proinflammatory chemokine IL-8. (WO 97/08324, Lau A. S.). An additional important and relevant recent finding was that LPS induction of the proinflammatory cytokines IL-6 and IL-12 was defective in PKR-null cells and impaired in PKR-null mice (Goh, et al., 2000). Thus, PKR is a key player in the cellular response to various stress signals that culminate in the synthesis of pro-inflammatory cytokines.

Activation of PKR has dualistic effects on cellular homeostasis. It results in the initiation of protein synthesis that inhibits pathogen/cancer growth, and concomitantly activates the transcription of proinflammatory cytokines and other genes. Taken together, these events limit pathogen invasion and favor the propagation of inflammatory responses to enhance immune defense.

Cytokines are soluble proteins produced during the activation of innate and acquired immune response to a variety of tissue insults including infection, cancer and autoimmunity. Cytokines have pleiotropic effects, acting on many cell types to modulate the host's immune response and are the principal means for intercellular communication during an insult. Cytokines initiate the inflammatory response and define the magnitude and nature of the immune response. However, overproduction of proinflammatory cytokines can result in extensive damage to host tissues, leading to morbid states, and in severe cases, eventual mortality of the host. Examples of inflammatory diseases include rheumatoid arthritis, inflammatory bowel disease, malignancy-associated cachexia and septic shock Abbas, A. K., et al.,Eds., Cellular and Molecular Immunology, 4$^{th}$ edition, WB Saunders Co., 246–415, 2000)). Other diseases where inflammatory cytokines may play a role include cerebral stroke, congestive heart failure and various inflammatory lung diseases such as adult respiratory distress syndrome Barone, F. C. and Feuerstein G. Z., *J. Cereb. Blood Flow Meta* 19:819–834, (1999); Torre-Amione, G., et al., *Drugs* 59:745–751, (2000); Christman, J. W., et al., *Chest* 117:1482–1487, (2000)).

Induction of many proinflammatory cytokines involves the activation of nuclear transcription factors, and NE-κB is a prototype of these regulatory factors (Baldwin, A. S.,*Ann. Rev. Immunol.* 14:649–681, (1996)). Binding sites for NF-κB are present in the promoter regions of cytokine genes important in inducing the inflammatory responses associated with the fore-mentioned diseases (Abraham, E., *Critical Care Med* 28:100–104, (2000)). Therefore, a common mechanism of many anti-inflammatory drugs is to suppress the production of one or more these proinflammatory cytokines through the suppression of signaling pathways such as those involving NE-κB (Handel, M. L., et al., *Clin Exp Pharmacol Physiol.* 27:139–144, (2000)).

Drug discovery in the area of anti-inflammatory compounds has the potential to identify novel compounds that are more effective and/or better tolerated than existing anti-inflammatory compounds. Another important criterion for selection of a target is that suppression of such target does not induce immediate or long term deleterious effects or toxicity to the host. Recent reports on PKR-knockout mice showed that deletion of the PKR gene does not cause inherent toxicity or compromise the survival of the said animals, with the exception of diminished antiviral response. Yet, embryonic fibroblast cells derived from these animals have much less proinflammatory response following endotoxin stimulation (Williams, 1999, Goh, et al., 2000). Thus targeting PKR suppression should be a safe approach to ameliorate inflammation without serious untoward effects.

PKR is an upstream regulator of NF-κB activation and proinflammatory cytokine synthesis and therefore is useful as a new target for the development of potentially novel anti-inflammatory drugs. Ideally, the drug discovery approaches that are used can be adapted to high-throughput screening (HTS), allowing large numbers of compounds, e.g., combinatorial library compounds, to be screened in a short time, and at a relatively low cost. To date, there is a need for a cell system for identifying candidate anti-inflammatory compounds by high throughput screening or other facilitated screening methods, in particular, a system to screen candidates to suppress PKR activation and its consequent induction of undesirable cytokines. The present invention addresses this need.

SUMMARY OF THE INVENTION

The invention includes, in one aspect, a cell line for use in screening test compounds for anti-inflammatory activity.

The cell line is a mammalian, preferably human, cell line capable of producing a selected cytokine associated with an inflammatory response in humans and having elevated cytokine regulatory factor levels and activity. The cell line is transfected with (i) a vector containing DNA encoding a cytokine regulatory factor under the control of a first promoter, and (ii) a vector containing DNA encoding a detectable-marker protein, under the control of a second promoter that is responsive to cytokine induction. Culturing the cells under culture conditions in which PKR is overproduced, and under conditons of cytokine induction, is effective to produce detectable, preferably high, levels of the detectable-marker protein. Addition to the cell culture of a test compound that results in a diminution of the detectable-marker protein is indicative of anti-inflammatory activity.

In exemplary embodiments, the first promoter is constitutive, and the second promoter, which is operably linked to the reporter gene, includes a promoter sequence associated with the gene encoding TNF-alpha, TNF-beta, IL-1 IL-6, IL-8 genes, or other inflammatory cytokine. An exemplary detectable-marker protein is green fluorescent protein (GFP).

In another aspect, the invention provides an in vitro method for screening test compounds for anti-inflammatory activity. In practicing the method, the above cells are cultured under conditions in which a cytokine regulatory factor is overproduced and cytokine production is stimulated, such that the detectable-marker protein, encoded by a cDNA driven by the promoter of the selected cytokine, is produced at elevated levels. After adding a test compound to the cells, diminution in the level of the detectable marker protein is measured, as evidence of ability of the test compound to suppress levels of the selected cytokine indirectly or indirectly due the suppression of a cytokine regulatory factor.

These and other objects and features of the invention will be more fully apparent when the following detailed description of the invention is read in conjunction with the accompanying drawings.

BRIEF DESCRIPTION OF THE FIGURES

FIGS. 5A and 5B show promoter sequences (SEQ ID NO:1-9) for a variety of inflammatory cytokines or their receptors, as identified in the figures.

DETAILED DESCRIPTION OF THE INVENTION

I. Definitions

Figure 1:
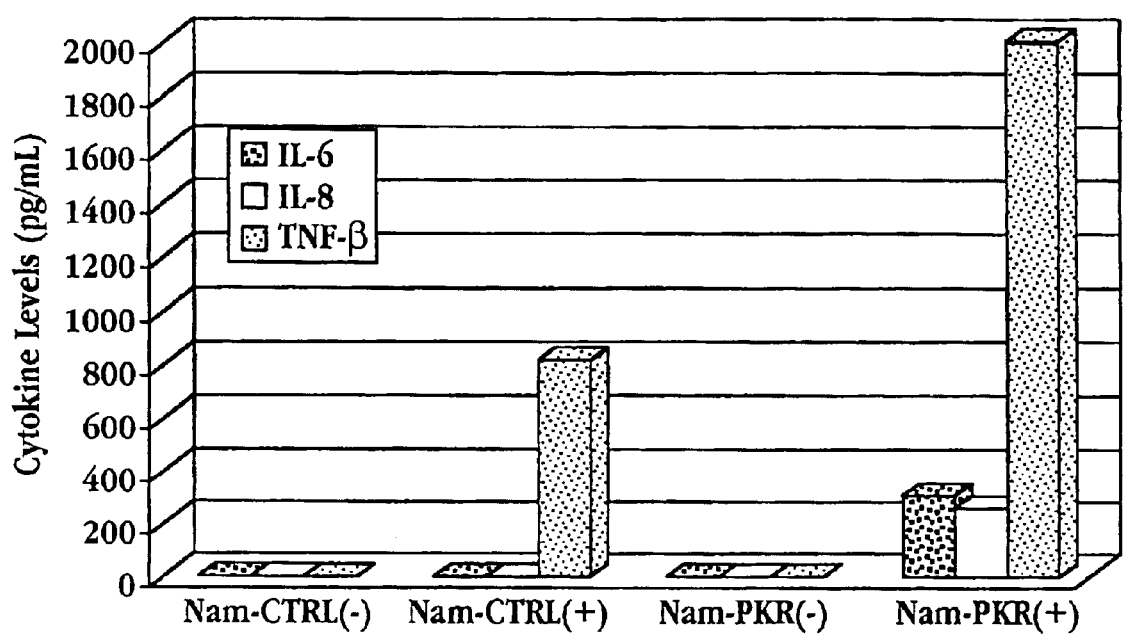
FIG. 1 shows interleukin-6 (IL-6), interleukin-8 (IL-8) and TNF-beta production with (Nam-Ctrl+) or without (Nam-Ctrl−) poly I:C treatment in untransformed parental Namalwa (Nam-Ctrl) and with (Nam-PKR+) or without (Nam-PKR−) poly I:C treatment in PKR-overexpressing Namalwa cells (Nam-PKR).

Unless otherwise indicated, all technical and scientific terms used herein have the same meaning as they would to one skilled in the art of the present invention. Practitioners are particularly directed to Sambrook et al., 1989, and Ausubel FM et al., 1993, for definitions and terms of the art. It is to be understood that this invention is not limited to the particular methodology, protocols, and reagents described, as these may vary.

The term "vector", as used herein, refer to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art. A cloning or expression vector may comprise additional elements, e.g., the expression vector may have two replication systems, thus allowing it to be maintained in two organisms, e.g. in human cells for expression and in a prokaryotic host for cloning and amplification. Cloning and expression vectors will typically contain a selectable marker gene.

The term "detectable-marker-encoding nucleotide sequence" or "detectable-marker gene" refers to a nucleotide sequence which is capable of expression in mammalian cells and where expression of the detectable-marker confers to cells containing the expressed gene the ability to grow in the presence of a detectable agent. The detectable-marker gene encodes a protein that (a) confers resistance to antibiotics or other toxins, e.g., ampicillin, neomycin, methotrexate, or tetracycline, (b) complements auxotrophic deficiencies, or (c) supplies critical nutrients not available from complex media, e.g., the gene encoding D-alanine racemase for Bacilli.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences ("control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. A promoter may be constitutive or inducible and may be a naturally occurring, engineered or hybrid promoter. Hybrid promoters combine elements of more than one promoter, are generally known in the art, and are useful in practicing the present invention.

The term "control sequences" refers to DNA sequences necessary for the expression of an operably linked coding sequence in a particular host organism. The control sequences that are suitable for prokaryotes typically include a promoter, optionally an operator sequence, and a ribosome binding site. Eukaryotic cells are known to utilize promoters, polyadenylation signals, and enhancers.

As used herein, the term "operably linked" relative to a recombinant DNA construct or vector means the nucleic acid sequence components of the recombinant DNA construct or vector are in a functional relationship with one another. Generally, "operably linked" DNA sequences are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

"Cells transfected with a vector" refers to cells which have been exposed to a vector, and have taken up the vector, either as a self-replicating genetic element or by integration into the cell genome, in a manner that allows expression of the protein(s) encoded by the vector. The expression may be under the control of a constitutive promoter in the vector, in which case protein expression occurs in the absence of an inducing agent, or under the control of an inducible promoter, requiring the presence of an inducer in the culture medium in order to achieve expression or high level expression of the vector gene.

As used herein, "recombinant" includes reference to a cell or vector, that has been modified by the introduction of a heterologous nucleic acid sequence or that the cell is derived from a cell so modified. Thus, recombinant cells exhibit modified gene expression, such as expression of genes not found in identical form within the native (non-recombinant) cell or expression of native genes that are otherwise abnormally expressed, underexpressed or not expressed at all, as a result of deliberate human intervention.

As used herein, the terms "transformed", "stably transformed" or "transgenic" with reference to a mammalian cell means the mammalian cell has a non-native (heterologous) nucleic acid sequence integrated into its genome which is maintained through two or more generations.

As used herein, the term "expression" refers to the process by which a polypeptide is produced based on the nucleic acid sequence of a gene. The process typically includes both transcription and translation, but in some cases may refer to transcription in the absence of translation.

The term "cytokine regulatory factor expression" refers to transcription and translation of a cytokine regulatory factor gene, the products of which include precursor RNA, mRNA, polypeptide, post-translation processed polypeptide, and derivatives thereof, and including cytokine regulatory factors from other species such as murine or simian enzymes.

It follows that the term "PKR expression" refers to transcription and translation of a PKR encoding nucleic acid sequence, the products of which include precursor RNA, mRNA, polypeptide, post-translation processed polypeptide, and derivatives thereof, and including PKRs from other species such as murine or simian enzymes.

As used herein, the terms "biological activity" and "biologically active", refer to the activity attributed to a particular protein in a cell line in culture. It will be appreciated that the "biological activity" of such a protein may vary somewhat dependent upon culture conditions and is generally reported as a range of activity. Accordingly, a "biologically inactive" form of a protein refers to a form of the protein that has been modified in a manner which interferes with the activity of the protein as it is found in nature.

As used herein, the terms "biological activity of a cytokine regulatory factor" and "biologically active cytokine regulatory factor" refer to any biological activity associated with the a particular cytokine regulatory factor or any fragment, derivative, or analog of that cytokine regulatory factor, e.g., enzymatic activity, etc.

As used herein, the terms "normal level of cytokine regulatory factor activity" and "normal level of cytokine regulatory factor expression" refer to the level of cytokine regulatory factor activity or expression, determined to be present in unmodified, uninduced, unprimed or uninfected cells of a particular type, e.g., the parental cell line of a particular type. It will be appreciated that such "normal" cytokine regulatory factor activity or expression, is reported as a range of cytokine regulatory factor activity or expression that is generally observed for a given type of cells which have not been modified by introduction of a cytokine regulatory factor-encoding nucleic acid sequence or selected for cytokine regulatory factor overexpression.

It follows that the terms "biological activity of PKR" and "biologically active PKR" refer to any biological activity associated with PKR, or a fragment, derivative, or analog of PKR, such as enzymatic activity, specifically including autophosphorylation activity and kinase activity involving phosphorylation of substrates such as eukaryotic translation initiation factor 2 (elF-2) and transcription factors such as NF-κB.

The range of "normal" cytokine regulatory factor activity or expression may vary somewhat dependent upon the cell line and culture conditions. For example, the U937 cell line may have a normal range of cytokine regulatory factor activity which differs from the normal range of cytokine regulatory factor activity for the Vero or Namalwa cell lines. It follows that over-expression of cytokine regulatory factor means an expression level which is above the normal range of cytokine regulatory factor expression generally observed for a given type of cells which have not been modified by introduction of a cytokine regulatory factor-encoding nucleic acid sequence or selected for cytokine regulatory factor overexpression, are unstimulated (not primed or induced) and are uninfected.

Accordingly, "overexpression" of cytokine regulatory factor means a range of cytokine regulatory factor activity, expression or production which is greater than that generally observed for a given type of cells which have not been modified by introduction of a vector comprising the coding sequence for PKR or selected for PKR overexpression, are unstimulated (not primed or induced) and are uninfected.

In one preferred aspect, cytokine regulatory factor overexpression means a level of cytokine regulatory factor activity, expression or production that is at least 125% (1.25-fold or 1.25×), preferably at least 150%, 200%, 300% or 400%, or 500% or more greater than the normal level of cytokine regulatory factor activity, expression or production for the same cell line under the particular culture conditions employed. In other words, a cell line that over expresses a cytokine regulatory factor typically exhibits a level of cytokine regulatory factor production or expression that is at least 1.25-fold and preferably 1.5-fold (1.5×), 2-fold (2×), 3-fold (3×), 4-fold (4×), 5-fold (5×) or more greater than the level of cytokine regulatory factor expression or production typically exhibited by the same type of cells which have not been selected, modified, primed or treated in a manner effective result in cytokine regulatory factor overexpression.

In some cases, a cell line that over expresses a cytokine regulatory factor such as PKR exhibits a level of cytokine regulatory factor expression or production that is 10-fold (10×) or more greater than the level of cytokine regulatory factor expression or production typically exhibited by the same type of cells under the particular culture conditions employed and which have not been selected, modified, primed or treated in a manner effective result in cytokine regulatory factor overexpression.

As used herein, the terms "normal level of cytokine" and "normal level of protein", relative to activity, expression, and production, refer to the level of cytokine or other protein activity, expression or production, determined to be present in parental cells of a particular type which have not been selected, modified, primed or treated in a manner effective result in cytokine regulatory factor overexpression. Examples include, a wild type ("parental") cell line which has not been selected, primed or treated in a manner to result in enhanced cytokine regulatory factor activity, expression or production, and a cell line which does not comprise an introduced cytokine regulatory factor coding sequence. It will be appreciated that such "normal" cytokine or other protein activity, expression, or production, is reported as a range of activity, expression, or production, typically observed for a given type of cells and may vary somewhat dependent upon culture conditions. "Cytokine associated with inflammatory activity" means a cytokine that is induced in a human, and present at above-normal levels, during an inflammatory response. Such cytokines include, without limitation, IFN-alpha, IFN-beta, IFN-gamma, IL-1, IL-2, IL-6, IL-8, IL-12, TNF-alpha and TNF-beta. "Cytokines" refers to a group of low-molecular-weight regulatory proteins that regulate the intensity and duration of the immune response by exerting a variety of effects on lymphocytes and other immune cells. "Cytokine-producing cells" refers to cells, typically blood cells, that secrete cytokines in vivo, and also in cell culture. Such cells include monocytes, macrophages, dendritic cells, B cells, endothelial cells, epithelial cells, $T_H1$ and $T_H2$ (T-helper cells), NK (natural killer) cells, eosinophilsmast cells, bone-marrow cells, fibroblasts, keratinocytes, osteoblast derived cells, melanocytes, platelets, various other immune system cells, pancreatic parenchmal cells, glial cells and tumor cells derived from such cell types.

The terms "modifying" and the term "cell line modification" as used herein relative to a cultured human cell line refer to introducing a heterologous nucleic acid sequence that encodes a cytokine regulatory factor and/or a heterologous nucleic acid sequence that encodes an anti-apoptotic protein into a parental human cell line. The coding sequence in the heterologous nucleic acid construct may be of heterologous or autologous origin.

"Selecting" cytokine regulatory factor overexpressing cells generally refers to subcloning, screening and selecting for cells that overexpress one or more cytokine regulatory factors and growing the cells to produce a cytokine regulatory factor overexpressing cell line.

Screening typically includes functional assays for biological activity, protein assays and assays for cytokine regulatory factor mRNA, as further described below.

The term "priming" as used herein relative to a cytokine regulatory factor overexpressing cell line typically refers to exposing the cells to any of a number of agents, such as phorbol myristate acetate (PMA) or interferon-β.

The terms "induction" and "inducing" as used herein relative to a cytokine regulatory factor overexpressing cell line typically refer to exposing cells to a microbial inducing agent, such as Sendai virus, encephalomyocarditis virus, Herpes simplex virus or Newcastle Disease Virus; or exposing the cells to at least one non-microbial inducing agent selected from the group consisting of poly(I):poly(C) (poly I:C), or poly r(I):poly r(C) (poly rIC), heparin, dextran sulfate, cycloheximide, Actinomycin D, sodium butyrate, calcium ionophores, phytohemagglutinin (PHA), lipopolysaccharide (LPS) and derivatives thereof, such as 3-deacyl LPS, and chondroitin sulfate.

The terms "treating" and "treated", as used herein relative to a cytokine regulatory factor overexpressing cell line generally refers to induction, but may be used with reference to priming and/or induction and/or exposure to an additional agent, e.g., DEAE Dextran.

The term "cytokine mixture" as used herein refers to a composition comprising two or more cytokines produced by a human cell line.

The terms "treating", "treatment" and "therapy" as used herein relative to a human subject or patient refer to curative therapy, prophylactic therapy, and preventative therapy.

II. Cytokine Regulatory Factors

A number of factors are known to be involved in the induction and/or enhanced expression of cytokines in cells, e.g., human cells. These factors include cytokine- and other protein-specific transcriptional regulatory factors, e.g. interferon regulatory factors (IRF-1, IRF-3 and IRF-7), cytokine receptors, nuclear factor κB (NF-κB), activator protein-1 (AP-1), nuclear factor IL-6 (NF-IL6), and in particular, PKR.

Enhancing the expression or activity of any of these factors will generally result in higher than normal expression of one or more cytokine-encoding genes. PKR is used as herein as an example of a protein capable of regulating cytokine and other protein expression; however, it will be understood that the invention contemplates any of a number of cytokine and protein enhancing factors (designated herein as "cytokine regulatory factors" or "CRF"), e.g., protein kinase C (PKC) inducers, TNF-α, GM-CSF, EGF and PDGF, G-CSF, TGF, TNF-alpha or TNF-beta, IL-1, IFNs (IFN-alpha, IFN-beta, IFN-gamma) or chemokines (IL-8, Macrophage inflammatory proteins [MIP-1a & -1b] and monocyte chemotactic proteins [MCPs]); other cellular signaling factors such as PMA, calcium ionophores, sodium butyrate or endotoxin; polyI: C, double-stranded RNA or viral analogs; PHA, cellular stress signals that can activate PKR, including heat shock, pathogen infection, e.g. viral infection; and any factor that enhances expression of a cytokine regulatory factor resulting in enhanced cytokine production.

By increasing the expression/activity of a cytokine regulatory factor in human cells, cytokine production can be increased. Human cell cultures that express a higher constitutive level of the cytokine regulatory factor, or in which cytokine regulatory factor expression can be induced to higher levels are therefore useful for the production of mixtures of cytokines.

The methods of the invention rely on the use of cells that overexpress a cytokine regulatory factor, with no particular method of cytokine regulatory factor overexpression required.

Various functions have been attributed to PKR, including, phosphorylation of eukaryotic initiation factor-2 (eIF- 2alpha), which, once phosphorylated, leads to inhibition of protein synthesis (Hershey, et al., 1991). This particular function of PKR has been suggested as one of the mechanisms responsible for mediating the antiviral and antiproliferative activities of IFN-alpha and IFN-beta. An additional biological function for PKR is its putative role as a signal transducer, for example, by phosphorylation of IkB, resulting in the release and activation of nuclear factor kB (NF-kB) (Kumar A et al., 1994).

It has previously been demonstrated that PKR mediates the transcriptional activation of IFN expression (Der D and Lau A S, 1995). Consistent with this observation, suppression of endogenous PKR activity by transfecting U937 cells with antisense to PKR or expression of a PKR-deficient mutant resulted in diminished induction of IFN in response to viral infection (Der D and Lau A S, 1995).

It has also been demonstrated that cells transfected with a PKR-encoding nucleic acid sequence exhibit enhanced interferon production, as described in co-owned U.S. Pat. No. 6,159,712.

It has also been suggested that PKR may function as a tumor suppressor and inducer of apoptosis. (See, e.g., Clemens M J et al., 1999; Yeung, Lau et al, 1996; Koromilas et al., 1992). Recent results indicate that expression of an active form of PKR triggers apoptosis, possibly through upregulation of the Fas receptor (Donze O, et al., 1999).

The invention employs cytokine-producing cells that overproduce a cytokine regulatory factor such as PKR by virtue of introduction of a cytokine regulatory factor-encoding nucleic acid sequence or by culturing non-transformed cells, or cells transformed with an apoptosis-inhibiting gene only, under conditions which produce above-normal levels of one or more endogenous cytokine regulatory factors. This may be accomplished by selection, priming and/or further treatment, such as induction.

With respect to PKR, additional approaches to enhanced production/expression include inactivation or decreasing the levels of the PKR-inhibiting factor, p58 which normally inhibits PKR activity. Mutation, modification or gene-targeting ablation of p58 has been shown to result in enhanced PKR activity (Barber, G. N. et al., 1994). Further, natural, synthetic or recombinant activators of PKR that can enhance the expression of PKR, e.g., the PKR activator protein, PACT (Patel, R. C. and Sen, G. C., 1998), may be employed.

III. Methods to Overexpress PKR and other Cytokine Regulatory Factors

According to an important feature of the invention, cells are transfected with two vectors. The first vector contains DNA encoding PKR under the control of a first promoter. One of the exemplary vectors shown in Example 1 is the pcDNA-PKR containing pcDNA encoding the full-length human PKR molecule (551 amino acids; Meurs, et al., 1990; GenBank Accession No. NM002759) inserted into a eukaryotic expression vector, such that the PKR coding sequence is expressed under the control of the CMV promoter. The vector contains various features suitable for PKR transcription and this vector is then cotransfected with another vector containing resistance gene markers to allow for selection and identification of the plasmids after co-transfection into eukaryotic cells.

The purpose of transfection with this vector is to achieve PKR overexpression in the cells, to enhance production of cytokines when the cells are cultured in the presence of agents known to stimulate cytokine production, as further described below.

IV. Nucleic Acid Constructs

A. Promoters

In one exemplary embodiment, a cytokine regulatory factor, e.g., PKR, is expressed under the control of a first promoter, which is constitutive, and a second promoter, which is operably linked to a reporter gene, includes a promoter sequence associated with the gene encoding an inflammatory cytokine.

A promoter is said to be "responsive to cytokine induction" if the promoter controls the expression of an inducible cytokine, that is, a cytokine whose level of expression is enhanced by an inducing agent, e.g., poly I:C or viral dsRNA. Typically, such a promoter is directly linked to the coding region of the inducible cytokine. Alternatively, the promoter may be linked to the gene for signaling factor, such as the gene for NF-kB, whose expression indirectly controls cytokine expression.

In general, vectors or plasmids are introduced into cells to develop cell lines for use in the methods of the invention. A first vector typically contains a promoter and a cytokine regulatory factor encoding nucleic acid sequence under the control of the promoter, together with suitable termination sequences, and a selectable-marker gene, e.g., geneticin, zeocin or a hygromycin resistance gene. The vector construction and transfection conditions are conventional, and known to those skilled in the art. In particular, it is well known, in such vector constructions, to obtain suitable plasmids or other vectors, e.g., from commercial sources, capable of being introduced into and replicating within selected human cells, where the plasmids may also be equipped with selectable markers, insertion sites, and suitable control elements, such as termination sequences.

Figure 4:
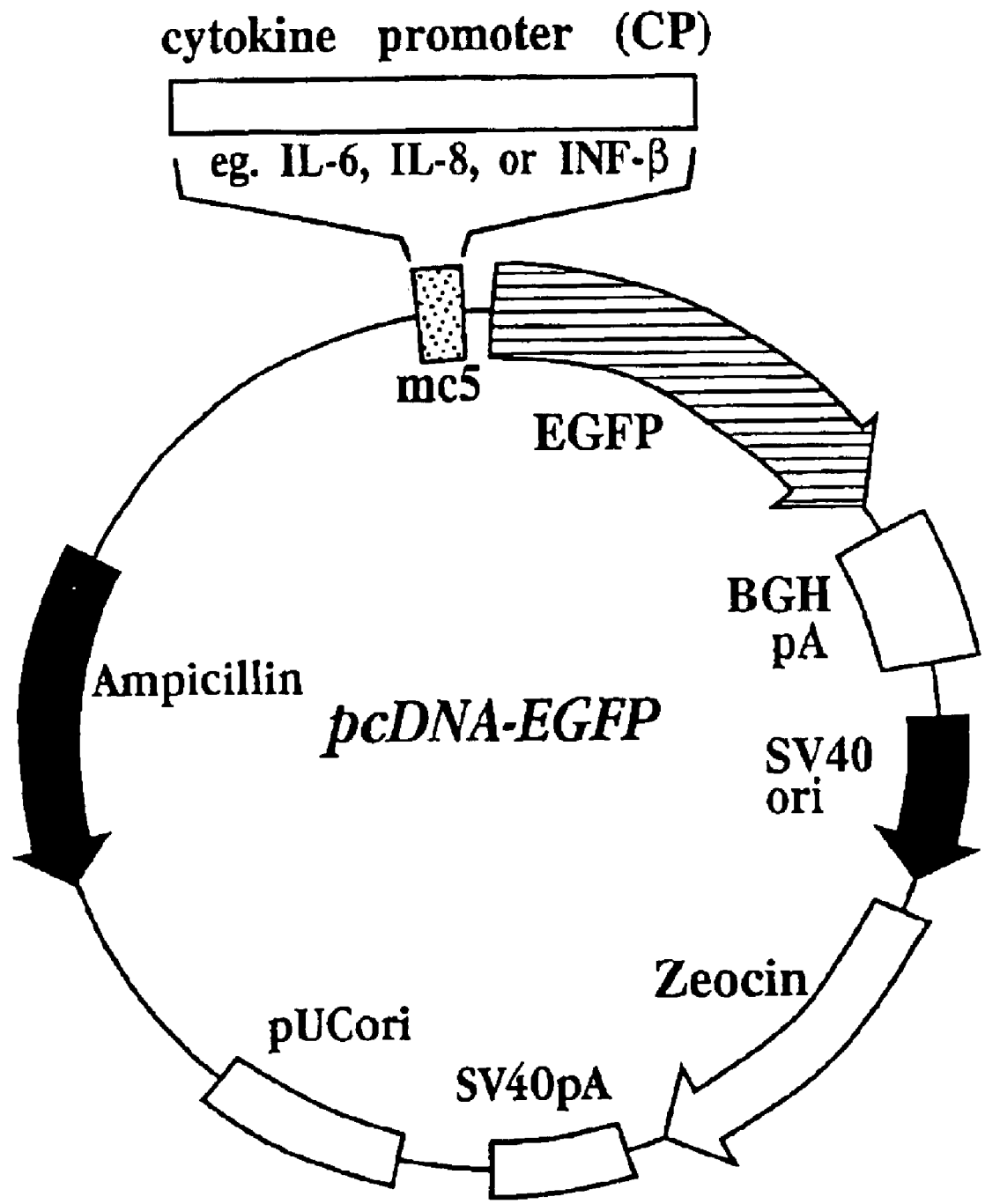
FIG. 4 is a diagram illustrating plasmid pcDNA-EGFP containing the enhanced green fluorescence protein (EGFP) cDNA in the sense orientation driven by an inflammatory cytokine promoter such as IL-6, IL-8 or TNF-beta.

The second vector, which contains the detectable-marker gene, is similarly constructed by known recombinant methods, such as given in Example 5 for the construction of the pcDNA-EGFP plasmid shown in FIG. 4. In addition to the expression vector elements detailed above, the second vector also contains a multiple cloning site (MCS) for introducing various cytokine promoters upstream of the EGFP. A selected resistance marker, e.g., hygromycin, is also inserted to allow for selection and identification of plasmids after transfer to eukaryotic cells, e.g., cells previously transfected with pCMV-PKR, a plasmid that contains a different selectable marker, e.g., neo.

The promoter inserted at the multiple cloning site (MCS) upstream of the EGFP in the plasmid is a promoter responsive to cytokine induction. Preferably, the sequence corresponds to or is derived from the promoter of the gene of an inflammatory cytokine, such as IL-1 GenBank Accession No. X03833; IL-2 GenBank Accession No. J00264; IL-3 GenBank Accession No. M60870; IL-6 GenBank Accession No. Y00081 or GenBank Accession No.AF005485 (partial sequence); IL-7 GenBank Accession No. XM_005266; IL-8 GenBank Accession No. M28130; IL-9 GenBank Accession No. M86593; IL-12 p35 GenBank Accession No. AF050083; IL-12 p40 GenBank Accession No. AY008847; IL-13 GenBank Accession No. U31120; IL-15 GenBank Accession No. XM_043810; IL-16 GenBank Accession No. AF121105; IFN-alpha GenBank Accession No. J00207; IFN-beta GenBank Accession No. V00534; IFN-gamma GenBank Accession No. J00219; TNF-alpha GenBank Accession No. X02910 or GenBank Accession No.L11698; and TNF-beta GenBank Accession No. M16441.

FIGS. 5A and 5B show promoter sequences (SEQ ID NO:1–9) for exemplary inflammatory cytokines or cytokine receptors, as identified in the figures, and which are suitable for use in the invention. Other suitable promoter sequences can be obtained from the GenBank database, or from literature references. The promoter sequences used include the portions of the sequences required for cytokine induction.

B. Cytokine Regulatory Factor Coding Sequences

A vector comprising a cytokine regulatory factor-encoding nucleic acid sequence may be introduced into a cell, resulting in expression of one or more cytokine regulatory factors by the cell.

Exemplary sequences encoding a cytokine regulatory factor for use in such vectors include, but are not limited to, the coding sequence from the human p68 PKR gene found at GenBank Accession No. M35663; the murine PKR gene and other eIF-2-alpha kinases including yeast GCN2 and hemin regulated inhibitor (Wek R C, Trends Biochem Sci 1994; 19: 491–496); 2-5A synthetase GenBank Accession No. NM006187; ISGγ3 GenBank Accession No. NM_002038; MxA GenBank Accession No. 30817;, MxB GenBank Accession No. 30818; IRF-1 GenBank Accession No. NM_002198; IRF-3 GenBank Accession No. NM_001571; IRF-7A GenBank Accession No. U53830; IRF7B GenBank Accession No. U53831; IRF-7C GenBank Accession No. U53832; cytokine receptors, NF-kB GenBank Accession No. NM_003998; AP-1 GenBank Accession No. J04111; NF-IL6 GenBank Accession No. X52560; PKC inducers, p38 MAPK GenBank Accession No. AF015256; Jak3 GenBank Accession No. NM_000215;, STAT GenBank Accession No. NM_007315; IFN-γ GenBank Accession No. J00219; IFN-β GenBank Accession No. V00534;; IFN-α GenBank Accession No. J00207; TNF-α GenBank Accession No. X02910; TNF-β GenBank Accession No. M16441; GM-CSF GenBank Accession No. NM_00758; G-CSF GenBank Accession No. X03655;, EGF GenBank Accession No. NM_001963; PDGFalpha GenBank Accession No. NM_002607; PDGFbeta GenBank Accession No. NM_002609; TGFbeta GenBank Accession No. M60316; IL-1, chemokines (IL-8 GenBank Accession No. M28130, MIP-1a GenBank Accession No. NM_002983, MIP-1b GenBank Accession No. J04130), monocyte chemotactic proteins (MCP1 GenBank Accession No. NM_002982), PMA, calcium ionophores, sodium butyrate or endotoxin, polyl: C, dsRNA, viral analogs, cellular stress signals that activate PKR, (heat shock, pathogen infection), factors that interact with a promoter controlling PKR expression, signal of transduction and transcription (STAT) and any factor that effects enhanced cytokine production.

In addition, mutants or variant forms of a cytokine regulatory factor-encoding nucleic acid sequence can be included in vector constructs for use in the overexpression of the cytokine regulatory factor. Upon expression, mutant or variant forms of these cytokine regulatory factors may have increased or decreased activity.

In accordance with the present invention, polynucleotide sequences or genes which encode cytokine regulatory factors include splice variants, fragments of the full length genes, coding sequences for fusion proteins, modified forms of native or full length genes or functional equivalents thereof, collectively referred to herein as "cytokine regulatory factor-encoding nucleic acid sequences".

A "cytokine regulatory factor-encoding nucleic acid sequence" may be incorporated into a recombinant DNA molecule or RNA viral vector (also termed a heterologous nucleic acid construct) with appropriate control sequences in order to direct the expression of the nucleic acid coding sequence in human cells.

Due to the inherent degeneracy of the genetic code, other nucleic acid sequences which encode substantially the same or a functionally equivalent amino acid sequence may be used to clone and express the CRF- or anti-apoptotic protein-encoding nucleic acid sequences. Thus, for a given CRF- or anti-apoptotic protein-encoding nucleic acid sequence, it is appreciated that as a result of the degeneracy of the genetic code, a number of coding sequences can be produced that encode the same amino acid sequence. For example, the triplet CGT encodes the amino acid arginine. Arginine is alternatively encoded by CGA, CGC, CGG, AGA, and AGG. Therefore it is appreciated that such substitutions in the coding region fall within the sequence variants covered by the present invention. Any and all of these sequence variants can be utilized in the same way as described herein for the native form of a CRF- or anti-apoptotic protein-encoding nucleic acid sequence.

A "variant" CRF- or anti-apoptotic protein-encoding nucleic acid sequence may encode a "variant" CRF- or anti-apoptotic amino acid sequence which is altered by one or more amino acids from the native polypeptide sequence, both of which are included within the scope of the invention. Similarly, the term "modified form of", relative to a CRF- or anti-apoptotic protein, means a derivative or variant form of the native CRF- or anti-apoptotic protein-encoding nucleic acid sequence or the native CRF- or anti-apoptotic amino acid sequence. Typically, a "modified form of" a native CRF- or anti-apoptotic protein or the coding sequence for the protein has a derivative sequence containing at least one amino acid or nucleic acid substitution, deletion or insertion, respectively.

The polynucleotides for use in practicing the invention include sequences which encode native CRF- or anti-apoptotic proteins and splice variants thereof, sequences complementary to the coding sequence and novel fragments of CRF- or anti-apoptotic protein encoding polynucleotides. The polynucleotides may be in the form of RNA or DNA, and includes messenger RNA, synthetic RNA and DNA, cDNA and genomic DNA. The DNA may be double-stranded or single-stranded and if single-stranded may be the coding strand or the non-coding (antisense, complementary) strand.

As will be understood by those of skill in the art, in some cases it may be advantageous to produce nucleotide sequences possessing non-naturally occurring codons. Codons preferred by a particular eukaryotic host (Murray, E. et al., 1989) can be selected, for example, to increase the rate of CRF protein expression or to produce recombinant RNA transcripts having desirable properties, such as a longer half-life than transcripts produced using the naturally occurring sequence.

A native CRF-encoding nucleotide sequence may be engineered in order to alter the coding sequence for a variety of reasons, including but not limited to, alterations which modify the cloning, processing and/or expression by a cell.

In one approach, a heterologous nucleic acid construct or expression vector for use in practicing the invention includes the coding sequence for a protein, the active form of which is desired such as the coding sequence for a cytokine regulatory factor (CRF), exemplified herein by PKR.

In one general embodiment of the invention, a CRF encoding nucleic acid sequence has at least 70%, preferably 80%, 85%, 90% or 95% or more sequence identity to the native coding sequence. For example, a coding sequence useful for expression of human PKR has at least 70%, preferably 80%, 85%, 90% or 95% or more sequence identity to the sequence found at GenBank Accession No. M35663.

Exemplary computer programs which can be used to determine identity between two sequences and thereby analyze variant coding sequences, include, but are not limited to, the suite of BLAST programs, e.g., BLASTN, BLASTX, and TBLASTX, BLASTP and TBLASTN, publicly available on the Internet on the NIH website. See, also, Altschul, S. F. et al., 1990 and Altschul, S. F. et al., 1997. Sequence searches are typically carried out using the BLASTN program when comparing a nucleic acid sequence relative to nucleic acid sequences in the GenBank DNA Sequences and other public databases. The BLASTX program is preferred for searching nucleic acid sequences which have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. [See, Altschul, et al., 1997.]

The degree of identity between two or more sequences in the analysis of variant coding sequences is generally performed using a sequence analysis program such as the CLUSTAL-W program (Thompson, J. D. et al., Nucleic Acids Research, 22:4673–4680. 1994) in MacVector version 6.5, operated with default parameters, including an open gap penalty of 10.0, an extended gap penalty of 0.1, and a BLOSUM 30 similarity matrix.

The relationship between two sequences may also be characterized by hybridization. A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. "Maximum stringency" typically occurs at about Tm-5° C. (5° below the Tm of the probe); "high stringency" at about 5–10° below the Tm; "intermediate stringency" at about 10–200 below the Tm of the probe; and "low stringency" at about 20–25° below the Tm. Functionally, maximum stringency conditions may be used to identify sequences having strict identity or near-strict identity; while high stringency conditions are used to identify sequences having about 80% or more sequence identity.

Moderate and high stringency hybridization conditions are well known in the art (see, e.g., Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2× SSC and 0.5% SDS at room temperature and two additional times in 0.1×SSC and 0.5% SDS at 42° C.

Cytokine regulatory factors for use in practicing the invention include, but are not limited to, ISG (2-5A synthetase, ISGγ3, Mx proteins), IRF-1, IRF-3, IRF-7, cytokine receptors, NF-kB, AP-1, NF-IL6, PKC inducers, p38 MAPK, STAT/Jak factors, IFN-γ, IFN-β, IFN-α, TNF-α, TNF-β, GM-CSF, G-CSF, EGF, PDGF, TGF, IL-1, chemokines (IL-8, MIP-1a &-1b), monocyte chemotactic proteins [MCPs], PMA, calcium ionophores, sodium butyrate or endotoxin, polyl: C, dsRNA, viral analogs, cellular stress signals that activate PKR, (heat shock, pathogen infection), factors that interact with a promoter controlling PKR expression, signal of transduction and transcription (STAT) and any factor that effects enhanced cytokine production.

C. Detectable-Marker Proteins

The detectable-marker gene in the vector encodes a protein whose presence and level in the cell can be measured, preferably quantitatively or semi-quantitatively. One preferred gene encodes for enhanced green-fluorescence protein (EGFP), as described in (Young et al., 1996). Levels of this protein can be easily determined by standard fluorometric methods, using as an example, an HTS7000 plate reader (Perkin Elmer) set at 488 nm as excitation and 511 nm as emission wavelengths (Heim and Tsien, 1966); Young et al., 1996). The vector generally includes the cytokine-responsive promoter, the GFP gene under the control of the promoter, and suitable termination sequences, as well as a detectable-marker gene used in initial selection of successful transformants. One exemplary detectable-marker protein is green fluorescent protein (GFP).

D. Introduction of Vectors into Cells

Vectors are the means by which DNA is delivered to the target cell. Methods known in the art for delivery of nucleic acid constructs into mammalian cells include viral methods using adenoviral vectors, retroviral vectors, or adeno-associated viral vectors. In general, the efficiency of gene transfer by viral vectors, e.g., retroviral vectors and adenoviral vectors, is higher than that of non-viral vectors. Retroviral vectors, including the most widely used amphotrophic murine leukemia virus (MuLV) vector, can infect only replicating cells, and typically, their transduction rate is lower than that of adenoviral vectors. However, since retroviral vectors integrate into the host genome the expression of the transgene is persistent. Recently retroviral vectors have been developed in which the therapeutic gene carrying vector construct is introduced into a packaging cell line that carries two independent constructs, which express structural proteins for packaging, thereby addressing safety issues surrounding the generation of replication competent retroviruses (Salmons and Gunzburg, 1997).

Adenoviral vectors can infect many cell types, resting and replicating, with high efficiency. Recently, a hybrid adeno/retroviral vector has been described. (See, e.g., Bilbao, et al., 1997.). Adeno-associated virus vectors also facilitate integration of transgenes into host chromosomes, and constitutive expression of a transgene, without evoking a strong host immune response.

Artificial chromosomes, e.g., yeast artificial chromosome (YAC) vectors may also be used to introduce heterologous nucleic acid constructs into cells.

Appropriate cloning and expression vectors for use in human cells are also described in Sambrook et al., 1989, and Ausubel F M et al., 1989, expressly incorporated by reference herein. The DNA coding sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Such vectors are typically equipped with detectable-markers, insertion sites, and suitable control elements, such as termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, and many are commercially available.

Detectable markers for use in such expression vectors are generally known in the art and the choice of the proper detectable marker will depend on the host cell. Typical detectable-marker genes encode proteins that confer resistance to antibiotics or other toxins, for example, ampicillin, methotrexate, tetracycline, neomycin (Southern and Berg, J., 1982), mycophenolic acid (Mulligan and Berg, 1980), puromycin, zeomycin, or hygromycin (Sugden et al., 1985).

V. Cell Compositions for Screening Compounds for Anti-Inflammatory Activity

Cell compositions useful for screening compounds for anti-inflammatory activity in vitro by suppressing PKR-mediated induction of proinflammatory cytokines are cytokine-producing cells which overexpress a cytokine regulatory factor and comprise the coding sequence for a detectable-marker protein expressed under the control of a cytokine promoter.

Cytokine-producing cells are transfected with the vectors by conventional methods, e.g., electroporation, as described in Example 2, and selected for successful transfection first by selection on a suitable selection medium, e.g., one containing geneticin, and then for expression of the inserted heterologous coding sequence—PKR or GFP, as detailed in Example 1, for the CMV promoter based PKR vector, as detailed in Example 5, for the pcDNA-EGFP vector. Successful transformants containing the first vector are selected on the basis of elevated PKR production. Successful transformants containing the second vector are readily selected on the basis of detectable levels of EGFP, following activation of PKR by inflammatory cytokines or agents such as poly I:C, IPS, or PMA and a PKR inducing agent such as 1) IFN-alpha, IFN-beta and other IFNs, GM-CSF, G-CSF, TGF, EGF, TNF-alpha or TNF-beta, IL-1; 2) other cellular signaling factors such as PMA, calcium ionophores, sodium butyrate or endotoxin ; 3) polyIC, double-stranded RNA or viral analog; 4) cellular stress signals that can activate PKR including heat shock or pathogen infections including virus.

VI. Cell Line Induction

A. Cell Lines

Any of a number of known cell cultures is useful as a parental strain for making a PKR-overproducing cell culture. Any cells normally capable of producing cytokines are suitable as the parental strain, particularly cells derived from fibroblasts or immune cells, including B cells, T cells, monocytes, neutraphils, natural killer cells, preferably human cells. Particularly suitable cell cultures are Namalwa (lymphoblastoid B) cells detailed in Example 2, pro-monocytic U937 cells, and MRC-5 (human fibroblast) cells. Also suitable are WI-38 cells, Flow 1000 cells, Flow 4000 cells, FS-4 and FS-7 cells, MG-63 cells, CCRF-SB cells, CCRF-CEM or Jurkat cells (T cells), WIL2 cells (B cells), or THP-1 cells (monocytes).

Cell lines comprising cells that have been selected, modified, primed and/or primed and induced in a manner effective to result in enhanced expression of one or more cytokine regulatory factors relative to the corresponding parental cell line (which is unmodified, unselected, unprimed and uninduced) are useful in practicing the present invention.

Examples of parental cell lines for use in practicing the present invention include, but are not limited to, B cells (Namalwa, 293, Raji), monocytic cells (U937, THP-1) , Vero, MRC-5, WI-38 cells, Flow 1000 cells, Flow 4000 cells, FS-4 and FS-7 cells, fibroblasts (MRC-5, MG-63 cells), CCRF-SB cells, T cells (CCRF-CEM, Jurkat) cells and T98G cells.

Examples of primary cell line for use in practicing the present invention include, but are not limited to, cells of the monocyte/macrophage lineage, lymphocytic lineage cells including T- and B-cells, mast cells, fibroblasts, bone marrow cells, keratinocytes, osteoblast derived cells, melanocytes, endothelial cells, platelets, various other immune system cells, lung epithelial cells, pancreatic parenchmal cells, glial cells and tumor cells derived from such cell types.

B. Culture Conditions

Cells useful for the production of mixtures of cytokines are cultured under conditions typically employed to culture the parental cell line. Generally, the cells are cultured in a standard medium containing physiological salts and nutrients, such as standard RPMI, MEM, IMEM or DMEM, F12 which may be supplemented with 5–10% serum, such as fetal bovine serum. Alternatively, serum free and/or protein-free medium may be used, a number of examples of which are commercially available such as Pro293 for example. Culture conditions are also standard, e.g., cultures are incubated at 37° C. in stationary or roller cultures until desired levels of cytokine production is achieved. For large scale production, fermentors may be used with cells grown in batch or a perfusion mode.

In general, preferred culture conditions for a given cell line may be found in the scientific literature and/or from the source of the cell line such as the American Type Culture Collection. Preferred culture conditions for primary cell lines, such as fibroblasts, B-cells, T-cells, endothelial cells, dendritic cells, and monocytes are generally available in the scientific literature. After cell growth has been established, the cells are exposed to conditions effective to cause or permit the overexpression of one or more cytokine regulatory factors, primed and/or primed and induced for enhanced production of mixtures of cytokines.

In cases where an exogenously provided cytokine regulatory factor-encoding nucleic acid sequence is provided under the control of an inducible promoter, the appropriate inducing agent, e.g., a metal salt or antibiotic, is added to the medium at a concentration effective to induce cytokine expression/production.

C. Cytokine Induction

The invention relies on the use of cell lines that have been selected, modified, primed and/or primed and induced in a manner effective to result in enhanced production of cytokines as compared to the corresponding untreated parental cell line. The selected cells are cultured under conditions of cytokine regulatory factor and cytokine overexpression and further comprise a vector which includes the coding sequence for a detectable-marker protein under the control of a promoter which is responsive to cytokine induction. The cells are used to screen test compounds for anti-inflammatory activity, by adding a test compound to the cultured cells and observing if there is any effect on the level of the selectable-marker protein.

Cell lines that have been selected have been obtained by the combination of limiting dilution cloning and screening in order to obtain a cytokine regulatory factor-overexpressing cell line. Alternatively, a cytokine regulatory factor-overexpressing cell line may be obtained by modifying a parental cell line capable of producing cytokines by introducing the coding sequence for a cytokine regulatory factor into cells of the parental cell line and selecting for a cytokine regulatory factor-overexpressing cell line.

Cell lines are primed by culturing in the presence of one or more priming agents. Priming agents for cytokine induction include, but are not limited to, (1) IFN-alpha, IFN-beta and other IFNs, GM-CSF, G-CSF, TGF, EGF, TNF-alpha or TNF-beta, IL-1; (2) other cellular signaling factors such as PMA, calcium ionophores, sodium butyrate or endotoxin ; (3) poly I:C, double-stranded RNA or viral analog; (4) cellular stress signals that can activate PKR including heat shock or pathogen infections including virus, that upregulate the endogenous levels of PKR and associated signaling molecules in the PKR pathway.

By way of example, a concentration of PMA in the range 5–50 nM, typically about 10 nM, is suitable. It will be understood that the optimal priming agent concentration and combination of priming agent, inducing agent and conditions for such priming and induction of a particular type of cells for production of a specific cytokine mixture will vary. However, such conditions may be determined by one of skill in the art without extensive experimentation.

Induction or treatment refers to the addition of a microbial, (viral, bacterial, or fungal) inducer, an extract of a microbe capable of acting as an inducer (e.g., an endotoxin or bacterial cell wall containing extract), or a non-microbial inducer to the cell culture. Exemplary non-microbial inducers include, but are not limited to, double-stranded RNA (dsRNA) such as poly(I):poly(C) or poly r(I):poly r(C) (poly I:C) or viral dsRNA such as Sendai virus RNA, small molecules, e.g., polyanions, heparin dextran sulfate, chondroitin sulfate and cytokines.

Exemplary methods of viral induction include, but are not limited to, (1) exposure to live virus (such as Sendai virus, encephalomyocarditis virus or Herpes simplex virus); (2) exposure to the aforementioned killed virus; or (3) exposure to isolated double-stranded viral RNA. In addition, cytokine induction may be produced or enhanced by adding particular cytokines known to stimulate cytokine production in certain cells.

After addition of the inducing agent, cells are generally further incubated until desired levels of induced and secreted cytokines are obtained. Incubation at 37° C. for at least 12–48 hours, and up to 72–96 hours is generally sufficient.

VII. Methods for Screening Compounds for Anti-inflammatory Activity in vitro

In accordance with another aspect of the invention, the cell lines described above are used to screen for compounds having anti-inflammatory activity, as evidenced by a test compound's ability to down-regulate a selected cytokine promoter.

In one exemplary application of the screening method, the above cells are grown under conditions of PKR overexpression and cytokine induction. Production of IL-6, IL-8 and TNF-beta by a PKR overexpressing Namalwa 41027 cell line is obtained by priming with phorbol myristate acetate (PMA), followed by induction with poly I:C. The cytokine producing cells are cultured in a suitable medium following induction of cytokine production. PKR-mediated cytokine induction, in turn, stimulates production of a detectable-marker protein under the control of the cytokine-or PKR-dependent responsive promoter, producing high (easily detectable) levels of the detectable marker, e.g., GFP. The level of detectable-marker protein establishes a baseline against which the potential anti-inflammatory activity of test compounds being screened will be assessed.

In another examplary experiment detailed in Example 3, the level of PKR expression in a parental and PKR overexpressing cell line is compared in a PKR activity assay (Zamanian-Daroush, et al., 1999). PKR expression by a PKR-transfected Namalwa cell line was approximately sixteen-fold greater than that of a parental Namalwa cell line. PKR-transfected Namalwa cells (Nam-PKR) and parental Namalwa cells (NAM-Ctrl) were treated with PMA and poly I:C for three days. The IL-6, IL-8 and TNF-beta expression level in the treated PKR-expressing and non-expressing cell lines were compared to the expression level of the same in a set of the same cell lines which were not treated with PMA and poly I:C. The data in FIG. 1 show an significant increase in the expression levels of IL-6, IL-8 and TNF-beta in the presence of inducing agents PMA and poly I:C in the PKR-overexpressing Namalwa cell line compared to the expression levels of the same in the parental Namalwa cell line and PKR-overproducing Namalwa cell line without treatment by PMA and poly I:C. Therefore, the experiment illustrates an effective method for monitoring the effects of anti-inflammatory drugs and inducing the production of inflammatory cytokines by activating PKR in a mammalian cell culture.

Figure 2A:
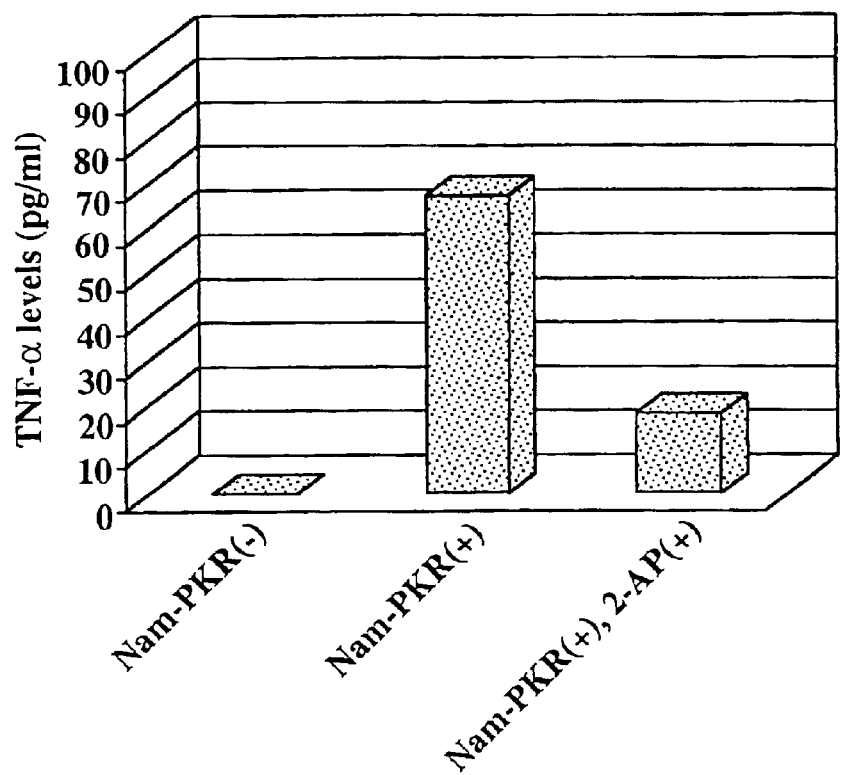
FIG. 2A shows the TNF-alpha production in PKR-overexpressing Namalwa cells with (Nam-PKR$^+$) and without (Nam-PKR$^-$) poly I:C treatment, and in PKR-overexpressing Namalwa cells treated with poly I:C and 2-aminopurine (2-AP).
Figure 2B:
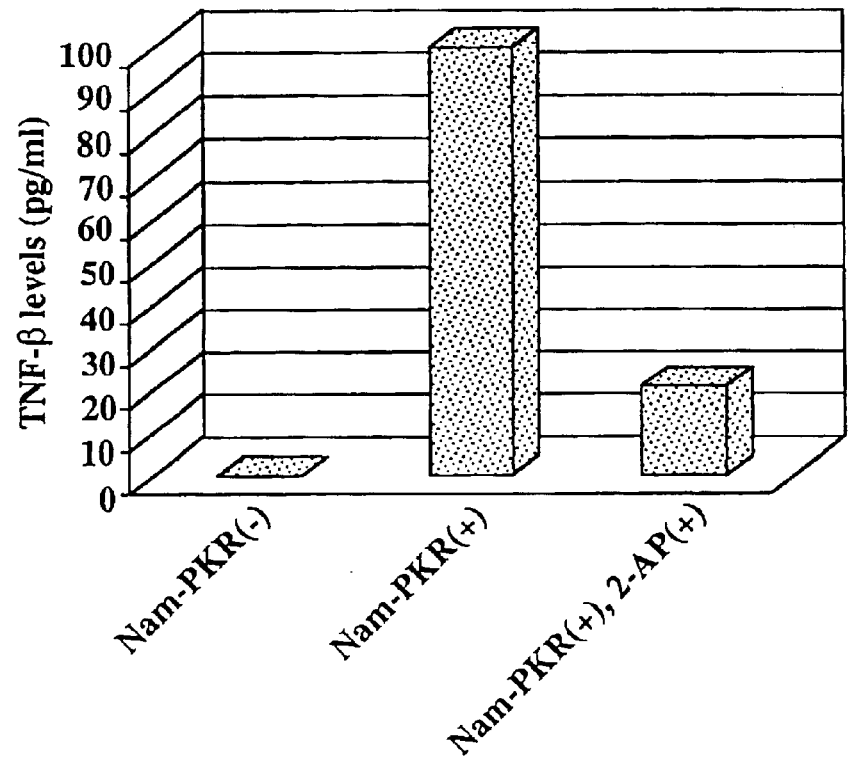
FIG. 2B shows the TNF-beta production in PKR-overexpressing Namalwa cells with (Nam-PKR$^+$) and without (Nam-PKR$^-$) poly I:C treatment, and in PKR-overexpressing Namalwa cells treated with poly I:C and 2-aminopurine (2-AP).

Once an elevated baseline level of marker protein is achieved, test compounds, such as 2 aminopurine (2 AP), are added to the culture in the presence of the inducer to determine the effect on the level of the selected cytokine (Example 4). The data in FIG. 2A show that the production level of TNF-alpha in the PKR overproducing Namalwa cell line was suppressed 4-fold in the presence of the PKR inhibitor 2 AP, compared to the TNF-alpha production level by the same cell line in the absence of the PKR inhibitor 2 AP. The data in FIG. 2B show analogous results, in which production level of TNF-beta was suppressed by 5-fold in the presence of the PKR inhibitor 2 AP. The above data demonstrate (i) that cytokine regulatory factor overexpression in cytokine-producing cells leads to enhanced expression of cytokines, and (ii) exposing of the cells to an agent effective to inhibit cytokine regulatory factor induced cytokine production is effective to significantly reduce the levels of induced cytokines.

Typically, a suspension of cultured cells is aliquoted into each of several wells, and increasing amounts of the test compound, e.g., 0, 10, 100, 1000, 10,000 mM are added to the wells. After a suitable incubation time, e.g., 2–6 hours, the level of the detectable marker protein in the wells is measured, to determine if the compound, at any concentration, has resulted in a diminution of detectable-marker protein, as evidence of the (i) inhibition by the compound of the level of the selected cytokine, and (ii) reduced expression protein of GFP due to downregulation of the cytokine-responsive promoter, directly or indirectly due to suppression of PKR activity, that is, suppression at some point in PKR pathway(s).

Compounds to be tested typically will include known anti-inflammatory compounds, such as glucocorticoids, salicylates, cyclosporin, rapmycin and the PKR inhibitor, 2-aminopurine and structural analogs thereof, such as analogs generated as part of a chemical library including known anti-inflammatory compounds, prostaglandin inhibitor or COX-2 inhibitors . Other candidates are small polypeptides of nucleic acid aptamer compounds, e.g., members of a polypeptide or DNA aptamer library.

Compounds identified as anti-inflammatory compound candidates may be further tested in defined screening systems, such as animal model systems, to further assess the potential of the compound as an anti-inflammatory agent.

Figure 3:
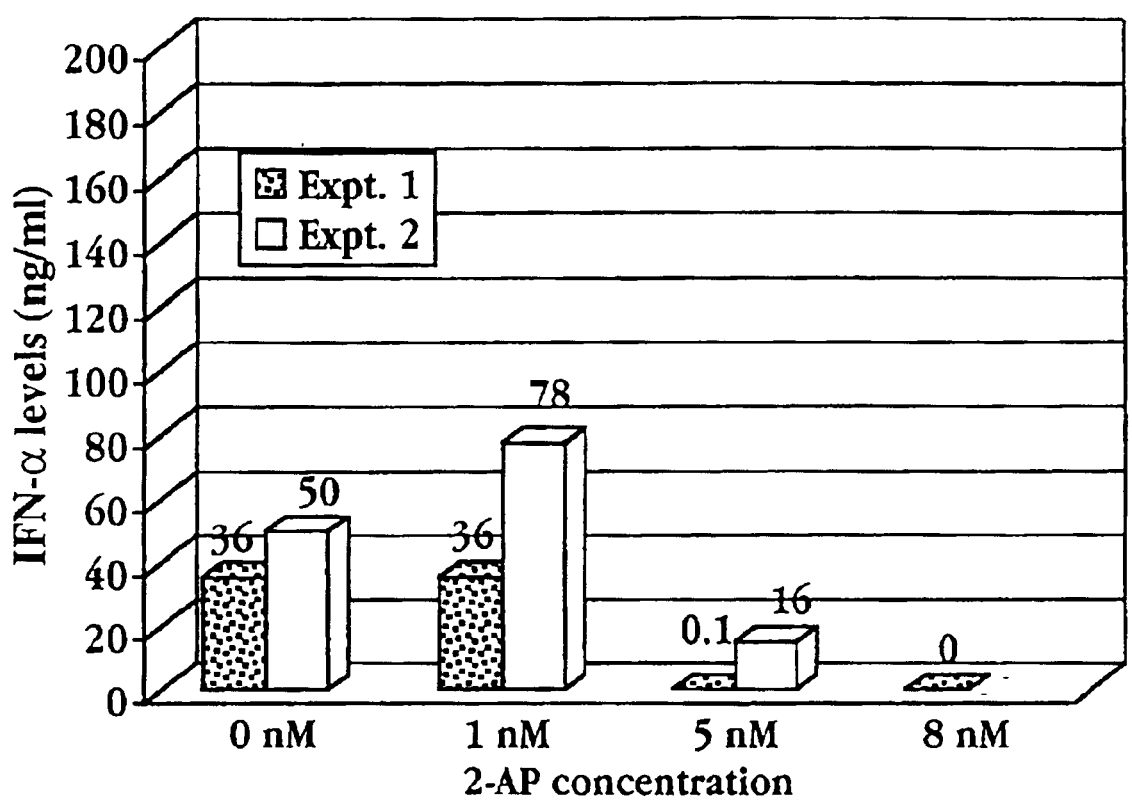
FIG. 3 shows the effect of various doses of 2-aminopurine (2-AP) on IFN-alpha production in PKR-overexpressing Namalwa cells (Nam-PKR).

The data in FIG. 3 show the effect of various concentrations of 2-AP on IFN-alpha production in PMA and poly r(I):poly r(C) treated PKR-overexpressing Namalwa cells (details of the experiment are in Example 4). The data from two independent experiments show that a significant inhibition of IFN-alpha occurs between 1 mM and 5 mM 2-AP, and that 1 mM was ineffective at inhibiting IFN-alpha production. A dramatic inhibition of IFN-alpha at 5 mM 2-AP relative to 1 mM (360-fold) and a corresponding 5-fold inhibition of INF-alpha production between 1 mM and 5 mM were detected in two experiments. At 8 mM 2-AP, IFN-alpha was completely inhibited. The dose response inhibition of IFN-alpha by 2-AP further demonstrates the feasibility of using the PKR-overexpressing Namalwa cell line to screen for potential anti-inflammatory drugs that target PKR.

It will be appreciated that the screening format is readily adaptable to high-throughput screening (HTS), for example, by simultaneously screening a large number of sample in the microtiter wells of a multiwell plate, such as one having 96, 720 or larger numbers of wells. The wells are readily assayed for compound effect, simply by assaying the level of the fluorescence from the cell samples at optimal fluorescence excitation and emission wavelengths. Test compounds which show evidence of producing a decreased color can then be retested for more precise dose response, to further determine the potential value of the compound as an anti-inflammatory compound.

When a test compound that (i) reduces the level of the detectable marker, and (ii) is active at a pharmaceutically practical level has been identified, the compound may be further assayed to develop its pharmacological profile. Such tests may include in vitro cell-culture studies to determine the effect of the identified compound in types of cytokine-producing cells, the ability of the identified compound to inhibit actual expression of a given pro-inflammatory peptide, with or without PKR overexpression, the ability of the compound to inhibit inflammation in suitable animal model systems, and the toxicology profile of the compound in animals.

In addition, when test compounds are identified, the compound may be further developed by standard drug-design or combinatorial-structure approaches to seek more active analogs, and/or compounds with reduced toxicity.

Specific examples of the steps described above are set forth in the following examples. However, it will be apparent to one of ordinary skill in the art that many modifications are possible and that the examples are provided for purposes of illustration only and are not limiting of the invention unless so specified.

EXAMPLE 1

Preparation of a PcCMV-PKR Vector and a PKR(−) Control Vector cDNA encoding the full-length human PKR molecule (551 amino acids; Meurs, et al., 1990; GenBank Accession No. NM002759) was inserted into a eukaryotic expression vector, such that the PKR coding sequence was expressed under the control of the CMV promoter.

The vector contains various features suitable for PKR transcription, including: i) a promoter sequence from the immediate early gene of the human CMV for high level mRNA expression; ii) a polyadenylation signal and transcription termination sequences from the β-globin gene to enhance RNA stability; iii) an ampicillin resistance gene and ColE1 origin for selection and maintenance in *E. coli*.

A second vector contained i) an ampicillin resistance gene and a ColE1 origin for selection and maintenance in *E. coli*; ii) the G418 resistance marker (Neo) to allow for selection and identification of the plasmids after co-transfection into eukaryotic cells.

EXAMPLE 2

Preparation and Analysis of a PKR Over-producing Namalwa Cell Line Over-expressing Inflammatory Cytokines Stable transfectants were obtained by electroporation of $4 \times 10^6$ exponentially growing Namalwa cells with 15 μg of the vector pCMV-PKR and 15 μg of the Neo containing second vector in DMEM/F12 (+10% FBS) using a Gene Pulser apparatus (BioRad) set at 800 μF, 300 V. Bulk populations of stable transformants were obtained by selection with 2 mg/ml geneticin (Gibco-BRL) for 3–4weeks. Clonal lines were subsequently obtained by limiting dilution cloning.

A. Increased Inflammatory Cytokine Expression Following Induction

The level of PKR in the parental and PKR-transfected Namalwa cells were analyzed by Western blot and PKR activity assay (Zamanian-Daroush, et al., 1999). PKR expression was found to have increased approximately sixteen-fold in the PKR-transfectants relative to the parental Namalwa cells.

PKR-transfected Namalwa cells (Nam-PKR) and parental Namalwa cells (Nam-Ctrl) were cultured at $2.5 \times 10^5$ cells/ml in DMEM/F12 medium supplemented with 10% FBS. The cells were treated with 20 mM PMA (priming) for 20 hr followed by treatment with 200 μg/ml poly r(I): poly r(C) (induction) for 3 days. One set of cells was left untreated (non-induced controls). Following treatment, the culture supernatants were collected and analyzed for interleukin-6 (IL-6), interleukin-8 (IL-8) and TNF-beta levels by ELISA according to the procedure provided by the supplier of the ELISA kits (R&D Systems).

The levels of production of IL-6, IL-8 and TNF-beta by control and PKR-transformed cells with and without cytokine induction are shown in FIG. 1. As shown in the figure, with the exception of TNF-beta production in induced control cells, cytokine production was only seen in PKR-overproducing, induced cells. In particular, PKR-transfected Namalwa cells treated with PMA and poly I:C produced greater than 300 pg/ml of IL-6, approximately 300 ng/ml of IL-8 and 2000 pg/ml of TNF-beta, which represents at least a 100-fold, 10-fold and 2.5-fold increase, respectively, in cytokine levels compared to the PMA and poly I:C-treated parental Namalwa cells.

EXAMPLE 3

Suppression of PKR-mediated Inflammatory Cytokine Production by a PKR-Specific Inhibitor and Potential Anti-inflammatory Drug A. Suppression of PKR-mediated Inflammatory Cytokine Production by 2 Aminopurine PKR-transfected Namalwa cells (Nam-PKR) were cultured at $2.5 \times 10^5$ cells/ml in DMEM/F12 medium supplemented with 10% FBS. The cells were treated with 20 mM PMA (priming) for 20 hr followed by treatment with 200 μg/ml poly I:C (induction) for 3 days in the presence of 1 mM 2-aminopurine (2-AP) or in the absence of 2-AP. One set of cells was left untreated (non-induced controls). Following treatment, the culture supernatants were collected and analyzed for TNF-alpha or for TNF-beta by ELISA according to the procedure provided by the supplier of the ELISA kits (R&D Systems). The data for cytokine induction is shown in FIGS. 2A and 2B, which illustrates that the PKR-overexpressing Namalwa cell line produces a high level of proinflammatory cytokine (TNF-alpha) under induction conditions (FIG. 2A) and that the induced levels of TNF-alpha are about 4-fold lower in the presence of the PKR inhibitor, 2-AP. Similar results were seen for the proinflammatory cytokine TNF-beta (FIG. 2B).

B. Dose-response Inhibition of IFN-alpha by 2-AP

FIG. 3 shows the effect of increasing concentrations of 2-AP on IFN-alpha production in PMA and poly r(I):poly r(C) treated PKR-overexpressing Namalwa cells. The results of two independent experiments show that a significant inhibition of IFN-alpha occurs between 1 mM and 5 mM 2-AP. In both cases, 1 mM was relatively ineffective in inhibiting IFN-alpha levels. In the first experiment a dramatic inhibition of IFN-alpha at 5 mM 2-AP relative to 1 mM (360-fold) was detected. In second experiment a 5-fold inhibition of INF-alpha production between 1 mM and 5 mM was also detected. At 8 mM 2-AP, IFN-alpha production was completely inhibited.

EXAMPLE 4
Preparation of Plasmids Containing EGFP with Cytokine Promoters Responsive to PKR Mediated Activation A. Preparation of Plasmid pcDNA-EGFP Plasmid pcDNA-EGFP was prepared from pcDNA3.1/Zeo(+) (Invitrogen) in two steps. First, the CMV promoter from plasmid pcDNA3.1/Zeo(+) was removed by restriction enzyme digestion with Bgl II and Bam HI followed by religation of the purified promoterless vector. Second, the EGFP cDNA was excised from plasmid pEGFP (Clontech) with Xba I restriction enzyme and ligated into the promoterless pcDNA3.1/Zeo(+) plasmid that was also digested with Xba I. Plasmids were isolated and analyzed for EGFP insertion in the proper orientation relative to the multiple cloning site (MCS) by Not I digestion.

FIG. 4 shows the promoterless vector, pcDNA-EGFP. The vector contains: i) a multiple cloning site for introducing various cytokine promoters upstream of the EGFP cDNA; ii) a polyadenylation signal and transcription termination sequence from the bovine growth hormone (BGH) gene to enhance mRNA stability; iii) a SV40 origin for episomal replication and simple vector rescue; iv) an ampicillin resistance gene and a ColE1 origin for selection and maintenance in $E.$ $coli$; v) the zeocin resistance marker to allow for selection and identification of plasmids after transfer to eukaryotic cells, in particular, cells already transfected with pCMV-PKR, the plasmid that contains a different detectable marker (Neo).

B. Preparation of Vectors Containing Different Cytokine Promoters Responsive to PKR Mediated Activation FIG. 4 also illustrates the multiple cloning site (MCS) insertion site for inserting a selected promoter sequence from an inflammatory-cytokine gene. In addition, specific elements within these promoters that are critical to binding inflammatory and cytokine related transcriptional activators (e.g. NF-κB, IRF-1, -3 and -7, AP-1 and the STAT family) can also be synthesized and subcloned into the MCS.

EXAMPLE 5
Preparation of EGFP-expressing Cell Lines Capable of Monitoring PKR Mediated by Inflammatory Cytokine Production A. Preparation of a Cell Line Transfected with Plasmid pcDNA-EGFP Stable transfectants were obtained by electroporation of $4 \times 10^6$ exponentially growing PKR-overproducing Namalwa with 15 μg of pcDNA-EGFP in DMEM/F12 (=10% FBS) using a Gene Pulser apparatus (BioRad) set at 800 μF, 300 V. Bulk populations of stable transformants were obtained by selection with 1 mg/ml zeocin (Invitrogen) for 3–4 weeks. Clonal lines were subsequently obtained by limiting dilution cloning. The level of PKR in successful transformants was confirmed as before by Western blot and PKR activity assays (Zamanian-Daryoush, M., et al. *Oncogene* 18:315–326, 1999)) and EGFP expression was monitored by fluorescence detection (Yang, T. T. et a., *Nucleic Acids Res.* 24:4592–4593, (1996)).

B. Preparation of Cell Lines Transfected with Vectors Containing Different Cytokine Promoters Responsive to PKR Mediated Activation Stable transfectants were obtained by electroporation of $4 \times 10^6$ exponentially growing PKR over producing Namalwa with 15 μg of pcDNA-EGFP plasmids containing different cytokine promoters responsive to PKR mediated activation in DMEM/F12 (+10% FBS) using a Gene Pulser apparatus (BioRad) set at 800 μF, 300 V. Bulk populations of stable transformants were obtained by selection with 1 mg/ml zeocin (Invitrogen) for 3–4 weeks. Clonal lines were subsequently obtained by limiting dilution cloning. The level of PKR in successful transformants was confirmed as before by Western blot and PKR activity assays (Zamanian-Daroush, et al., 1999) and EGFP expression was monitored by fluorescence detection (Yang, et al., 1996). The invention now being fully described, it will be apparent to one of ordinary skill in the art that many changes and modifications can be made thereto without departing from the spirit or scope of the described invention.

---

What is claimed is:

1. A method for screening test compounds for anti-inflammatory activity, comprising:
   (a) culturing a mammalian cell line capable of producing a selected cytokine associated with an inflammatory response in humans, and transfected with (i) a vector comprising DNA encoding a cytokine regulatory factor under the control of a first constitutive promoter, and (ii) a vector comprising DNA encoding a detectable-marker protein, under the control of a second promoter which is responsive to cytokine induction, under culture conditions in which the cytokine regulatory factor is overproduced in the transfected cells, the selected cytokine is induced, and the detectable-marker protein is produced at detectable levels,
   (b) adding a test compound to the cultured cells, and
   (c) observing any diminution in the level of the detectable-marker protein.

2. The method of claim 1, wherein the cytokine regulatory factor is a mammalian double stranded RNA-activated protein kinase PKR.

3. The method of claim 2, wherein the cytokine regulatory factor is a human PKR.

4. The method of claim 1, wherein the second promoter is the natural promoter of the selected cytokine.

5. The method of claim 1, wherein the second promoter is the promoter associated with the human gene for TNF-alpha.

6. The method of claim 1, wherein the delectable marker protein is green fluorescent protein (GEP).

7. The method of claim 1, wherein said culturing further comprises adding to the cultured cells, an amount of a double stranded RNA (dsRNA) effective to stimulate cytokine production in the cytokine overproducing cells in culture.

8. The method of claim 1, wherein said culturing comprises adding to the cultured cells, priming agent PMA.

* * * * *